United States Patent [19]
Jacobsen et al.

[11] Patent Number: 5,888,235
[45] Date of Patent: Mar. 30, 1999

[54] BODY-POWERED PROSTHETIC ARM

[75] Inventors: Stephen C. Jacobsen, Salt Lake City; David F. Knutti, Taylorsville, both of Utah

[73] Assignee: Sarcos, Inc., Salt Lake City, Utah

[21] Appl. No.: 779,456

[22] Filed: Jan. 7, 1997

[51] Int. Cl.⁶ .................................. A61F 2/54; A61F 2/58
[52] U.S. Cl. ............................................... 623/58; 623/59
[58] Field of Search .......................................... 623/57–56

[56] References Cited

U.S. PATENT DOCUMENTS

| | | | |
|---|---|---|---|
| 1,385,817 | 7/1921 | Dilworth | 623/58 |
| 1,989,960 | 2/1935 | Wheeler et al. | 623/60 |
| 2,442,530 | 3/1948 | Eberle et al. | |
| 2,528,464 | 4/1950 | Wilkerson et al. | |
| 2,537,338 | 1/1951 | Fishbein et al. | 623/58 |
| 2,537,551 | 10/1951 | Sansbury | 623/57 |
| 2,572,914 | 10/1951 | Chapman et al. | 623/60 |
| 5,549,712 | 8/1996 | Gammer et al. | 623/57 |

*Primary Examiner*—John G. Weiss
*Assistant Examiner*—Bruce E. Snow
*Attorney, Agent, or Firm*—Thorpe, North & Western, L.L.P.

[57] ABSTRACT

A body-powered prosthetic arm is mountable on a socket attached to the arm stump of a person. The prosthetic arm includes a base for attachment to the socket, a forearm section having a proximal end and a distal end, a terminal device such as a hook, anthropomorphic hand, etc. attached to the distal end of the forearm section for selectively opening or closing, and an elbow joint for joining the proximal end of the forearm section to the base, the elbow joint being pivotable to enable moving the forearm section upwardly or downwardly. Control straps and cables fitted on the person are responsive to body movements of the person for selectively locking the elbow joint to prevent it from pivoting while allowing the terminal device to open or close or locking the terminal device to prevent it from opening or closing while allowing the elbow joint to pivot.

8 Claims, 11 Drawing Sheets

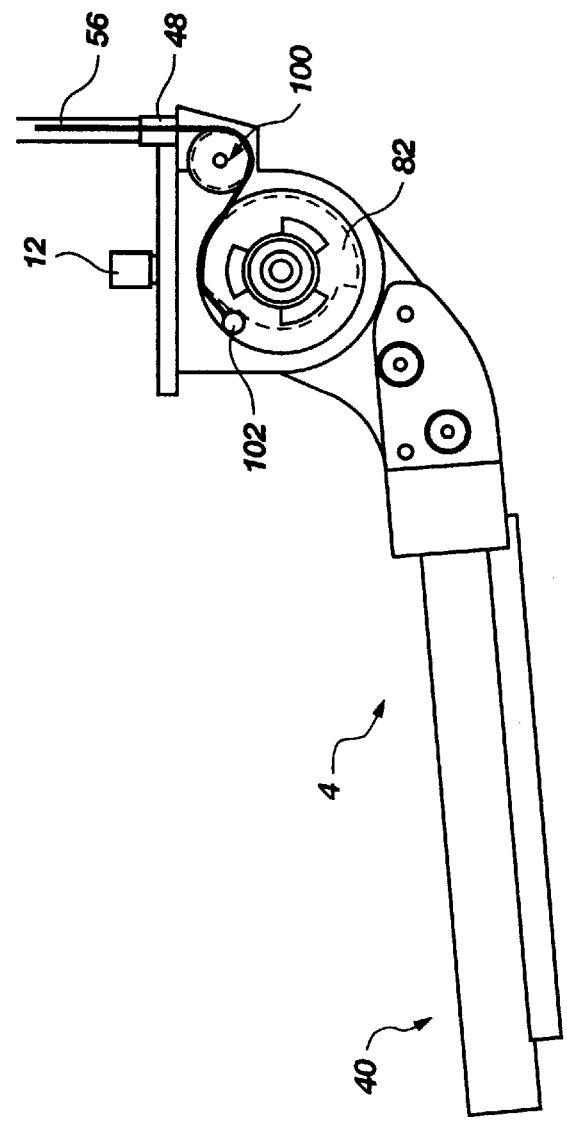
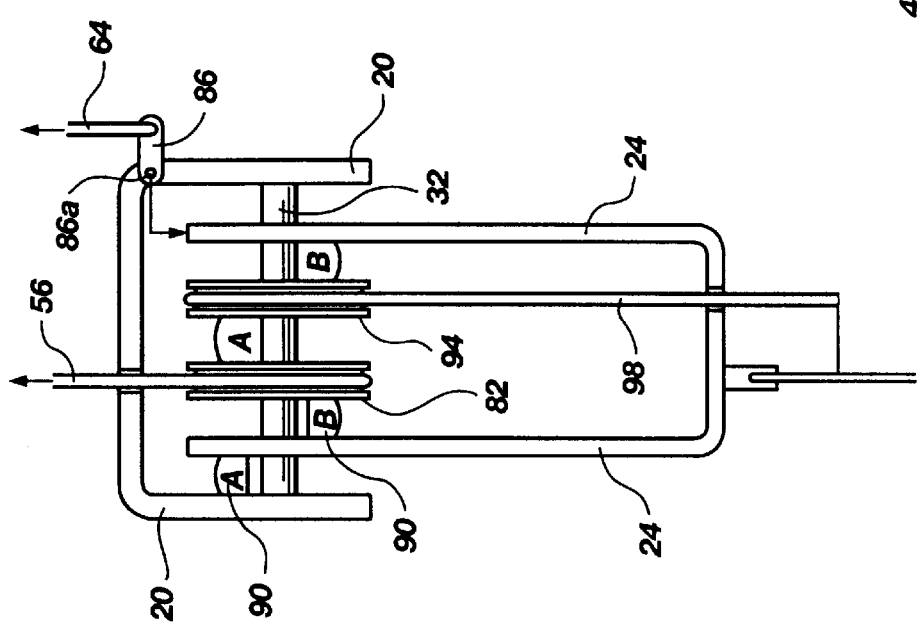

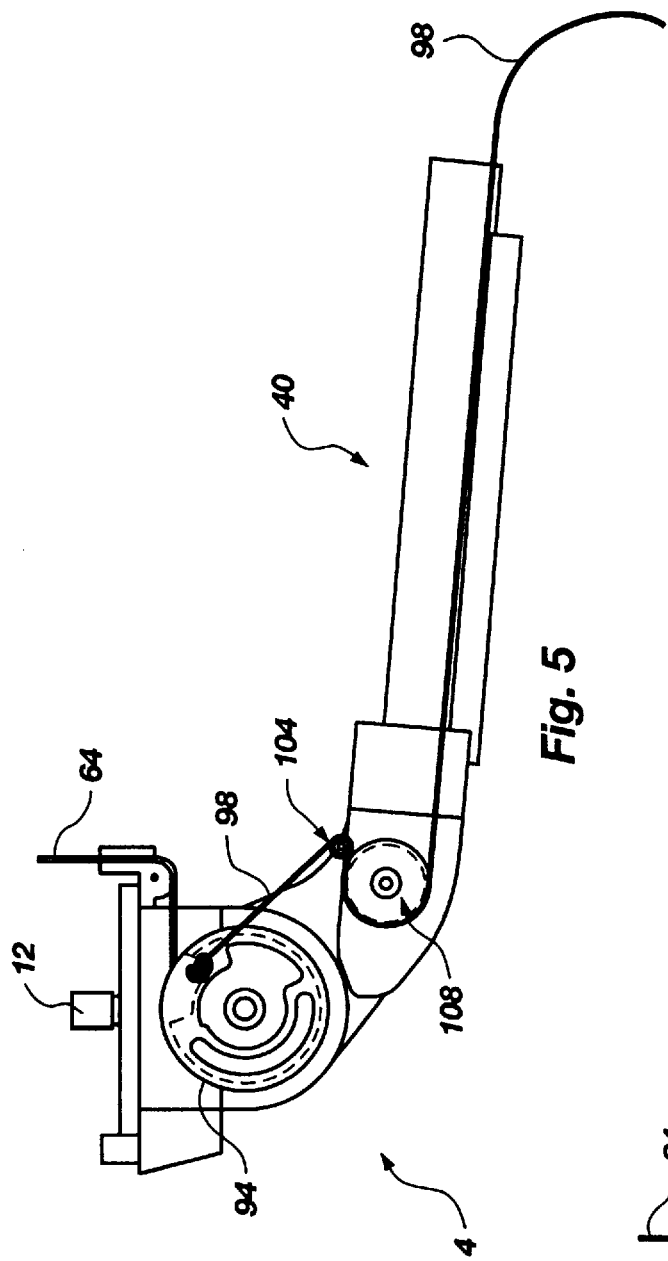
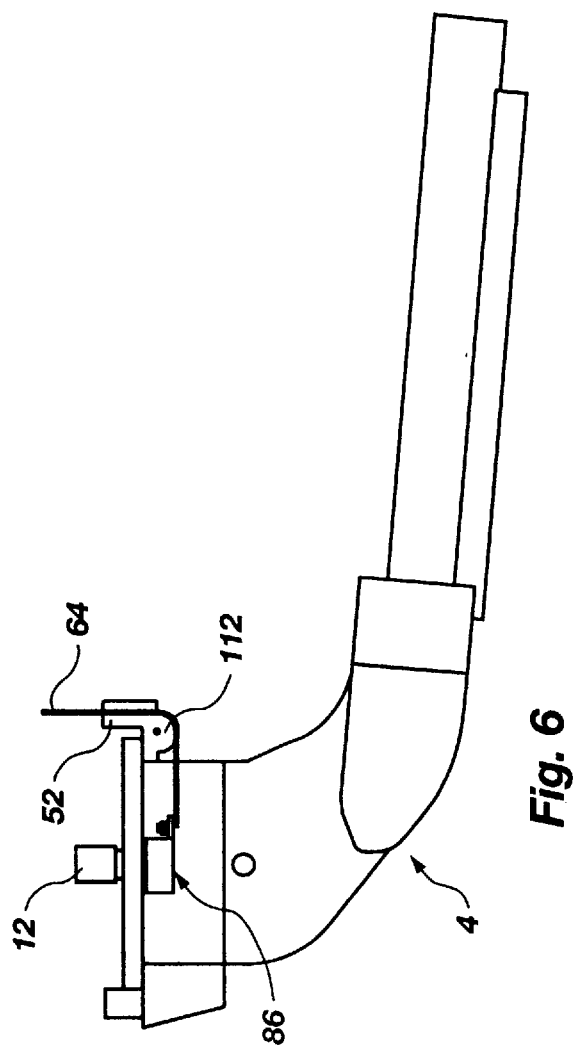

BODY-POWERED PROSTHETIC ARM

BACKGROUND OF THE INVENTION

This invention relates to a prosthetic arm and more particularly to a body-powered prosthetic arm having a bendable elbow and a terminal gripping device, each of which may be operated independently of the other, but with the same actuation mechanism.

Prosthetic arms generally fall into two categories, these being body-powered arms and motor-actuated arms. The body-powered type prosthetic arm is more widely used because it is less expensive, less complicated in design, does not require batteries, is lightweight, and is more reliable. The motor-actuated type prosthetic arm, however, does provide ease of use and some versatility in the operation of the gripping terminal device as to opening and closing of the gripping element and the pressure applied by the gripping element in grasping an object.

One of the most common body-powered prosthetic arm utilizes what is called a dual cable harnessing system, such as a figure eight harness, for attachment to a person's body and for actuating both the bending of the elbow portion of the arm and the opening and closing of the gripping element, typically a hook. One of the cables in this type system is for enabling one of the two possible movements to take place, i.e., either the bending of the elbow or opening or closing of the hook. The other cable is for causing the bending of the elbow or the opening or closing of the hook, whichever is enabled.

One of the problems with the above dual cable system is that with certain positions of the prosthetic arm, the two possible movements cannot be "decoupled", i.e., the bending of the elbow cannot be "decoupled" from the opening of the hook. Also, in certain other positions, there is insufficient length of actuation cable to effect an opening of the hook when desired. Such is the case, for example, when the hook is raised a certain distance toward the mouth and there is simply no more cable to enable opening the hook to release the object being held.

SUMMARY OF THE INVENTION

It is an object of the invention to provide a highly efficient body-powered prosthetic arm.

It is also an object of the invention to provide such a prosthetic arm which is inexpensive to manufacture, easy to service and replace parts, and is highly reliable.

It is a further object of the invention to provide such a prosthetic arm in which the function of bending the elbow is completely decoupled and independent from the function of opening or closing the gripping device.

It is still another object of the invention to provide such a prosthetic arm which may be easily installed and removed from a user.

It is also an object of the invention to provide such a prosthetic arm having capabilities of being moved close to the upper body of the wearer.

The above and other objects of the invention are realized in a specific illustrative embodiment of a body-powered prosthetic arm mountable on an arm stump of a person. The arm stump is fitted with a conventional socket on which the prosthetic arm is mounted. The prosthetic arm includes a connector end for mounting on the socket, and a forearm section having a proximal end, for pivotally attaching to the connector end to allow pivoting upwardly or downwardly of the forearm section, and a distal end on which a terminal device (such as a hook, anthropomorphic hand, etc.) is mounted. The arm also includes a locking mechanism responsive to movement of a cable for selectively locking in one state and preventing the pivoting of the forearm section, or locking in another state and preventing operation of the terminal device. A first cable is attachable to the body of the person and moveable when the body is moved in a certain way to thereby cause selective locking of the locking mechanism. A second cable is also attachable to the body of the person and to the forearm section and terminal device so that when the second cable is moved as a result of a certain movement of the body, the forearm section is caused to pivot if the terminal device is locked, or the terminal device is caused to operate if the forearm section is locked.

In accordance with one aspect of the invention, a lift assist element is coupled between the attachment member and the forearm section to provide a lifting force to the forearm section to at least partially compensate for the effects of gravity on the arm.

In accordance with another aspect of the invention, the forearm section is positioned at an angle with respect to the attachment member to provide a higher than normal lift elevation when the forearm section is pivoted upwardly.

BRIEF DESCRIPTION OF THE DRAWINGS

The above and other objects, features and advantages of the invention will become apparent from a consideration of the following detailed description presented in connection with the accompanying drawings in which:

FIG. 3 is a top, schematic view of a cable/pulley actuation mechanism suitable for use in the prosthetic arm of the present invention;

FIG. 4 is a schematic side view of the prosthetic arm of the present invention showing routing of the actuation cable;

FIG. 5 is a schematic side view of the prosthetic arm of the present invention showing the routing of the terminal gripping device cable;

FIG. 6 is a schematic side view of the prosthetic arm of the present invention showing the routing of the lock control cable;

DETAILED DESCRIPTION

Figure 1:
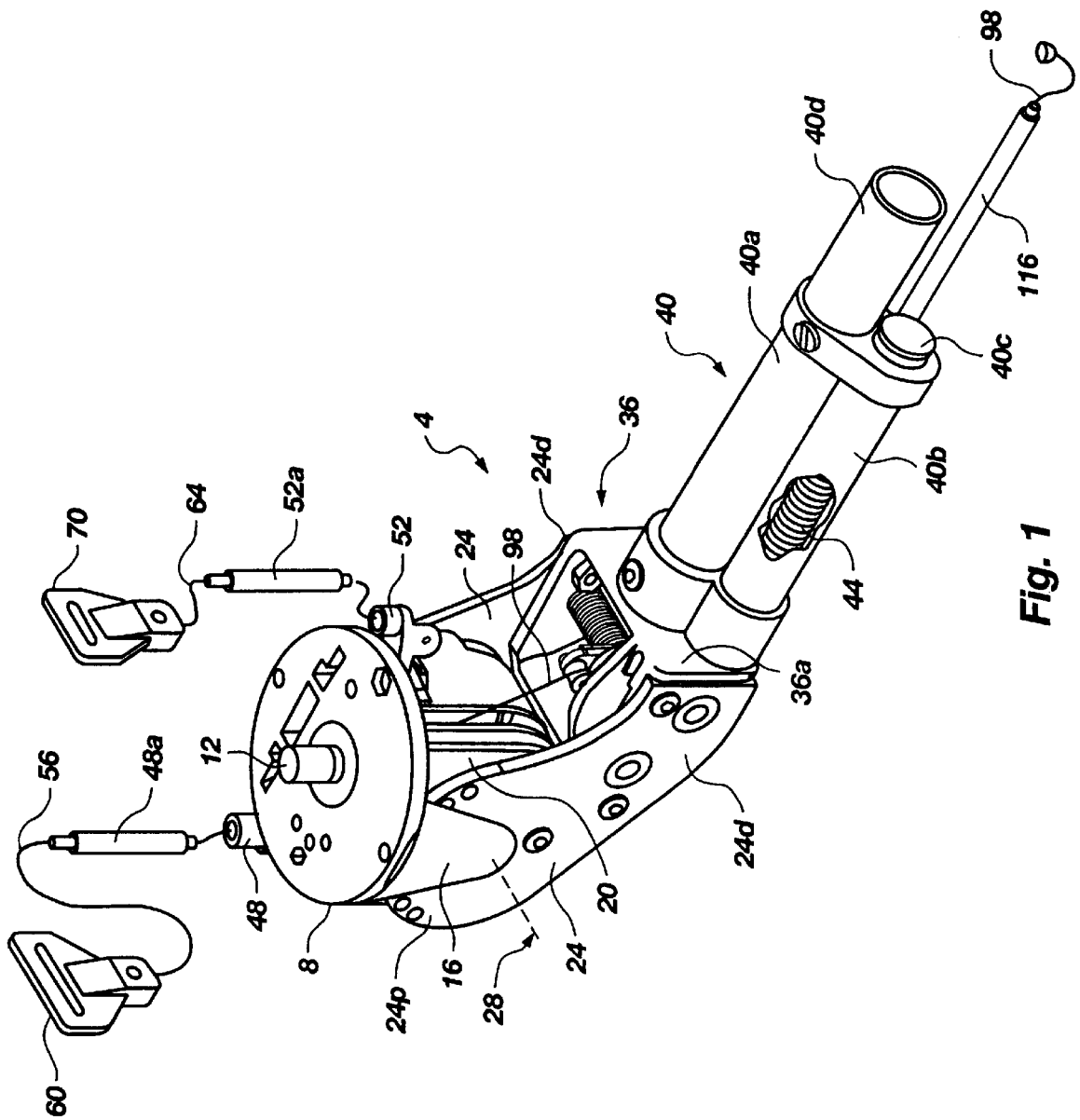
FIG. 1 is a perspective view of a body-powered prosthetic arm made in accordance with the principles of the present invention.
Figure 7:
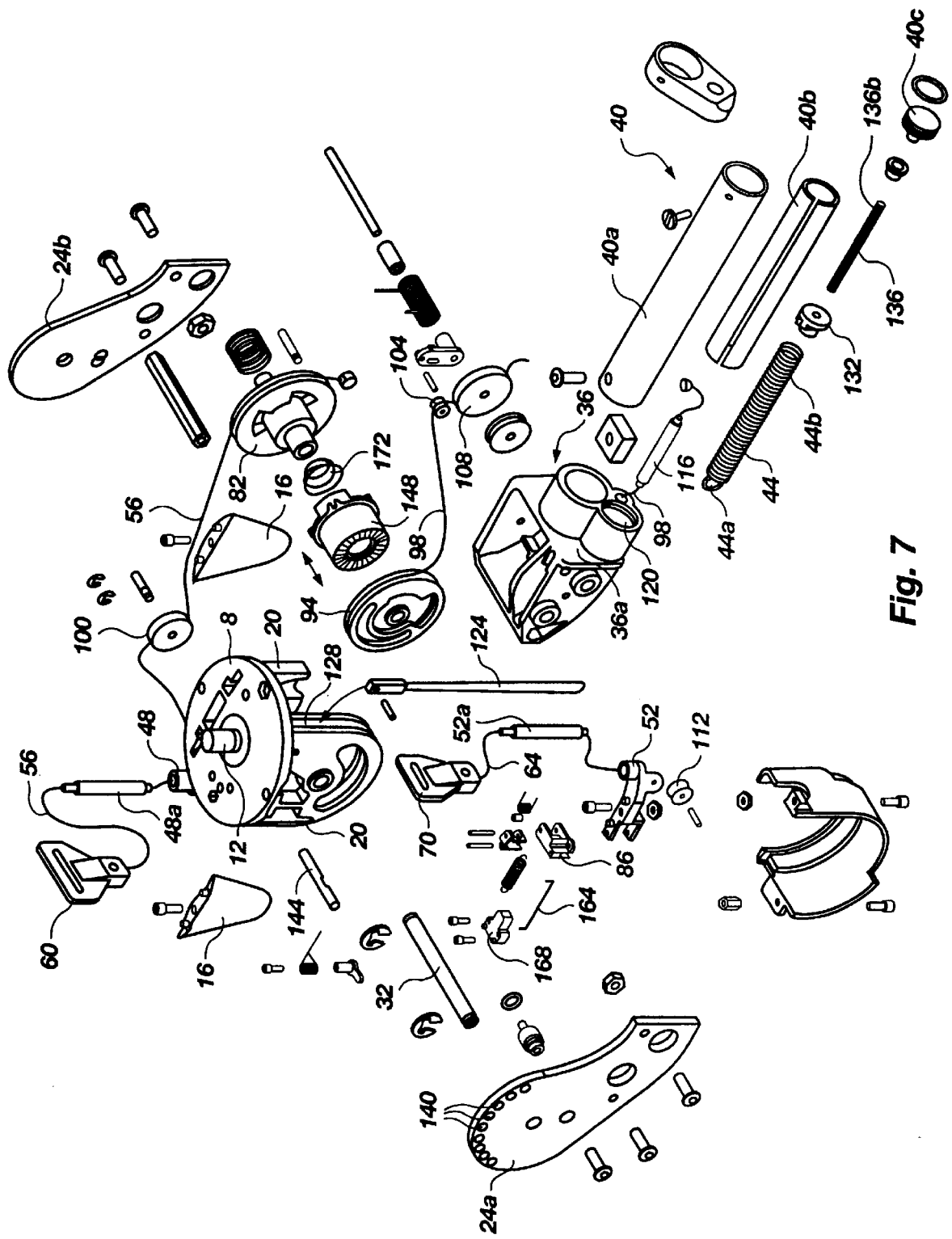
FIG. 7 is an exploded view of the prosthetic arm of FIG. 1.

FIG. 1 shows a perspective view of a prosthetic arm 4 made in accordance with the present invention. The arm 4 includes a base element or platform 8 on which a post 12 is mounted for receiving a socket fitted over the arm stump of an above-elbow amputee. Extending downwardly from the base 8, at spaced apart locations, are a pair of fairings 16 which cover a clevis 20 (FIG. 7) on the outside of which are received for pivotal attachment a pair of elbow plates 24. The elbow plates 24 include pivot ends 24p at which the elbow plates are attached to the clevis 20 to pivot upwardly and downwardly about an axis 28, represented by pivot shaft 32 (FIG. 7). The pivot shaft 32 extends between the clevis and the elbow plates 24 are pivotally mounted thereon.

The elbow plates 24 also include distal ends 24d to which the proximal end 36 of a forearm member 40 is attached. The proximal end 36 of the forearm member 40 is composed a pulley housing 36a in which are rotatably mounted a number of pulleys to be discussed later. Extending forwardly of the pulley housing 36a are a forearm tube 40a, onto the end of which various gripping elements or terminal devices may be fitted (FIG. 2), and a spring tube 40b in which a gravity compensation, lift assist spring 44 is disposed. The lift assist spring 44 provides compensation for the effects of gravity on the forearm 40 to provide a lift force to the forearm. The lift assist spring 44 is attached at a forward end to an adjustment knob 40c, to allow for shortening or elongating the spring to thus vary the lift force, and at a rearward end to a cable which is attached to the clevis 20. In this manner, the lift spring 44 assists in raising the forearm 40 relative to the clevis 20 and base 8.

The elbow plates 24 also include an intermediate section advantageously extending downwardly and forwardly of the pivot section 24p to a forward termination 24d. The forward termination 24d is connected to the forearm member 40. The intermediate section preferably forms a bend at an angle of between about 90 degrees and 180 degrees from the pivot section. More preferably, the intermediate section forms a bend of about 145 degrees. Thus, the forearm member is positioned at an angle with respect to the base element to provide a higher than normal lift elevation when the forearm section is pivoted upwardly. Therefore, the forearm may be moved closer to the upper body of the wearer.

Mounted on the edge of the base 8 are a pair of cylindrical cable guides 48 and 52 in which are fitted respectively cable housings 48a and 52a. A so-called power cable 56 is threaded through the cable housing 48a and cable guide 48 into the prosthetic arm to provide for raising or lowering the forearm 40, or for opening or closing a gripping element, to be discussed momentarily. The free end of the cable 56 is coupled to a conventional strap loop 60 which is coupled to a conventional shoulder strap 61 worn by the person on which the prosthetic arm is fitted.

A control cable 64 is threaded through the cable housing 52a and cable guide 52, into the prosthetic arm 4 for operating a state lock mechanism for selectively locking either the elbow plates 24 in place relative to the base 8 while allowing a gripping element to be opened or closed, or locking the gripping element in fixed position while allowing the elbow plates to be pivoted relative to the base, as will be further explained later. The free end of the control cable 64 is also coupled to a strap loop 70 which, in turn, is attached to a conventional shoulder strap 71 worn by a person for effectuating control of the state locking element and the prosthetic arm.

Figure 2:
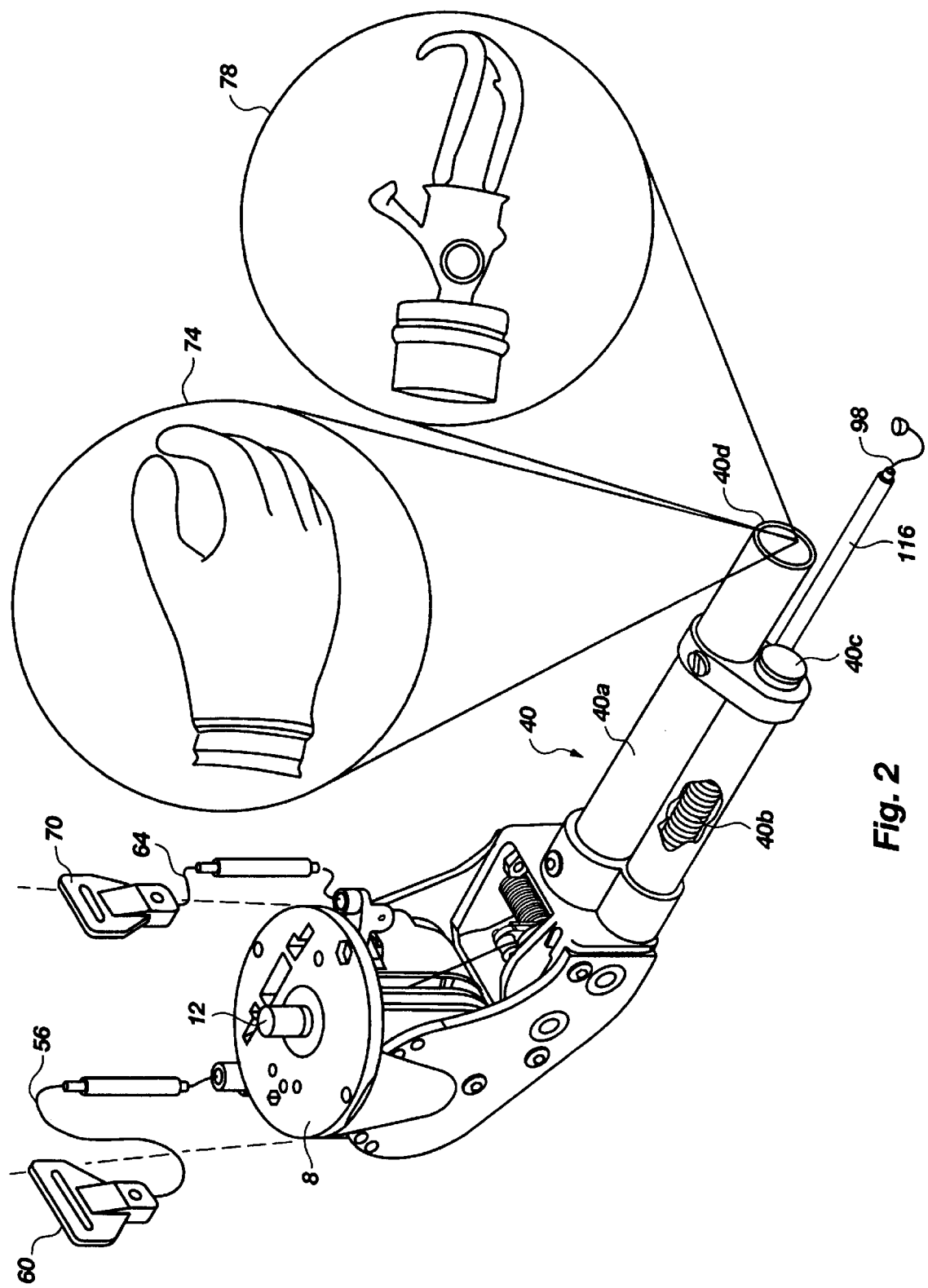
FIG. 2 is a perspective view of the arm of FIG. 1, but also showing two possible terminal gripping devices which could be installed on the arm.

FIG. 2 shows alternative terminal devices, one in the form of an anthropomorphic mechanical hand 74 and the other in the form of a hook 78, which may be fitted onto the distal end 40d of the forearm member 40. Both illustrative terminal devices 74 and 78 are conventional in the field of prosthetic parts, and both have the ability when operated to move between opened and closed positions, all in a conventional fashion. As will be evident later on, the power cable 56 is utilized to selectively open or close the terminal device installed on the forearm 40. (Typically, an elastic band or similar element causes closing of a terminal device, with the opening of the device being effectuated by pulling back on a cable.)

Referring now to FIG. 3, the power cable 56 is shown extending to and about an elbow actuating pulley 82 which, in turn, is mounted on the pivot shaft 32 extending between the clevis 20. The control cable 64 is shown coupled to a switch lever 86 which, when moved or toggled about a pivot axis 86a, causes a state lock mechanism represented schematically at 90 to change states between what will be referred to as either "hook lock" for elbow operation or "elbow lock" for hook operation (although other terminal devices could be employed other than a hook).

Also mounted on the pivot shaft 32 are the elbow plates 24, to which the forearm (not shown in FIG. 3) is attached. A hook actuating pulley 94 is also mounted on the pivot shaft 32 and a hook actuating cable 98 is wrapped thereabout and extends forwardly for attachment to the hook (or other terminal device) for effectuating opening or closing of the hook.

When the control cable 64 is pulled, causing the switch lever 86 to pivot, the state lock mechanism 90 is caused to change states either to the "elbow lock" state or the "hook lock" state. The next time the switch lever 86 is pivoted, the state lock mechanism 90 is caused to change states again.

The state lock mechanism 90 allows for locking the elbow or elbow plates 24 in any one of a plurality of angular positions relative to the clevis 20. This will be described further in connection with FIG. 7.

When the state lock mechanism 90 is in the "elbow lock" state, in which the elbow plates 24 are "locked" to the clevis 20 and the hook actuating pulley 94 is "locked" to the elbow actuating pulley 82, the elbow plates 24 are prevented from moving relative to the clevis 20. However, when the power cable 56 is moved to cause rotation of the elbow actuating pulley 82, the hook actuating pulley 94 is also caused to rotate to thereby move the hook actuating cable 98 and thus operate the hook, i.e., either open or close the hook.

When the state lock mechanism 90 is in the "hook lock" state, the elbow plates 24 are locked to both the elbow actuating pulley 82 and the hook actuating pulley 94 so that when the power cable 56 is moved and thus the elbow actuating pulley 82 is rotated, the elbow plates 24 are caused to move thereby causing the hook actuating pulley 94 to rotate. In effect, the hook actuating pulley 94 is maintained in the same angular position relative to the elbow plates 24 so that there is no operation of the hook. However, rotation of the elbow actuating pulley 82 causes the elbow plates 24 to pivot about the pivot shaft 32 to effectuate "bending" of the elbow, as desired.

FIG. 4 is a side, elevational, graphic view of the prosthetic arm 4 of FIG. 1, showing the power cable 56 extending downwardly through a cylindrical cable guide 48 and about a power idler pulley 100. From there, the power cable 56 extends forwardly and upwardly over the elbow actuating pulley 82 where it is affixed to the perimeter thereof at location 102.

As can be seen in FIG. 4, when the power cable 56 is moved upwardly, the pulley 82 is caused to rotate clockwise, in the direction in which the forearm member 40 would be caused to rise. Alternatively, when the power cable 56 is moved downwardly, the pulley 82 is allowed to rotate counterclockwise, in the direction in which the forearm member 40 would be allowed to move downwardly.

FIG. 5 is a side, elevational, graphic view of the prosthetic arm 4 of FIG. 1, showing the hook actuating cable 98 fixed at one end to the perimeter of the hook actuating pulley 94. The hook actuating cable 98 extends from there about a tension take-up pulley 104 and then about a hook cable pulley 108 to ultimately extend beside the forearm member 40 to a hook or other terminal device (not shown). The tension take-up pulley allows the maintenance of constant cable extension required for operating the hook, regardless of orientation of the forearm 40.

As can be visualized from FIG. 5, when the hook actuating pulley 94 is caused to rotate counterclockwise, the hook actuating cable 98 is pulled rearwardly of the forearm member 40 to operate (open) the hook, and when the hook actuating pulley 94 is caused to rotate clockwise, the hook actuating cable 98 moves forwardly of the forearm member 40 to cause the hook (or allow the hook) to close.

FIG. 6 shows a side, elevational, graphic view of the prosthetic arm 4 of FIG. 1. There shown is the control cable 64 extending through cable guide 52, under a control cable pulley 112, to the switch lever 86. Successive pulling of the control cable 64 causes the state lock mechanism 90 (FIGS. 3, 8 and 9) to switch between the "elbow lock" state and the "hook lock", as before described.

FIG. 7 shows an exploded view of the prosthetic arm of FIG. 1, with the principal parts numbered as described in connection with earlier figures. The power cable 56 is shown extending about power idler pulley 100 and over elbow actuating pulley 82. Similarly, hook actuating cable 98 is shown extending from hook actuating pulley 94 over the tension take-up pulley 104 and under the hook cable pulley 108. From there, the hook actuating cable 98 extends through a sleeve 116 for connection to the terminal device provided for the prosthetic arm.

The lift assist spring 44 is fitted in spring tube 40b which, in turn, is fitted in opening 120 in the pulley housing 36a. End 44a of the lift assist spring 44 is joined to a lift assist spring cable 124 which, in turn, is attached to one of the clevis 20 members and, in particular, is inserted in gap 128 in that one member. The other end 44b of the lift assist spring 44 is fitted with a plug 132 having a threaded opening therein, into which is screwed an adjustment bolt 136. Coupled on the distal end 136b of the bolt 136 is the adjustment knob 40c (previously discussed) which, when rotated, causes the bolt 136 to rotate in the threaded opening of the plug 132 to thereby either draw the end of the spring 44b closer to the knob 40c or move it further away. In this manner, the length of the lift assist spring 44 may be varied to thereby vary the lift assist force applied to the forearm 40.

As discussed earlier, the prosthetic arm 4 of the present invention has two lock states—a "hook lock" state and a "elbow lock" state. In the "elbow lock" state, the elbow plates 24 may be selectively locked in any one of a plurality of angular positions relative to the base 8. In particular, elbow plate 24a includes nine openings 140 into which a lock pin 144 may be inserted to lock the elbow plates 24 in a certain angular position. The lock pin 144 is moved by the state lock mechanism 90 (FIGS. 3, 8 and 9) into whatever one of the openings 140 is in alignment therewith at the time the lock mechanism is operated to effectuate the "elbow lock" state. This will be discussed in further detail in conjunction with FIGS. 8A and 8B and FIGS. 9A through 9E.

Figure 8B:
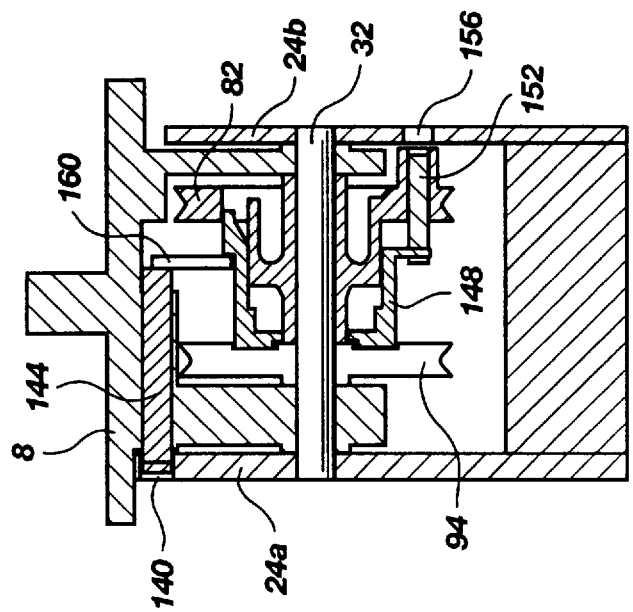
FIGS. 8A and 8B are front, cross-sectional views of the locking mechanism of the prosthetic arm of the present invention, in the "elbow lock" state and "hook lock" state, respectively.
Figure 8A:
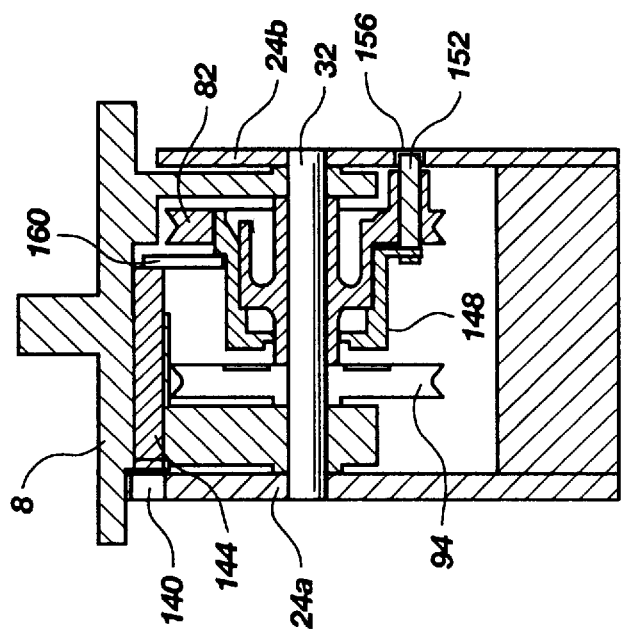

FIGS. 8A and 8B show front, cross-sectional views of the locking mechanism in the "hook lock" state and "elbow lock" state, respectively. Note that the position of the elbow actuating pulley 82 and hook actuating pulley 94 are switched from the positions shown in FIG. 3. In FIG. 8A, the "hook lock" state, a rachet 148 which is mounted on pivot shaft 32 and coupled to elbow actuating pulley 82, is out of contact with hook actuating pulley 94. In this position, a lock pin 152 which is mounted in the sliding rachet 148, is positioned to extend into an opening 156 in elbow plate 24b so that elbow actuating pulley 82 may not rotate relative to the elbow plates 24. Also, lock pin 144 is not in any of the openings 140 in the elbow plate 24a and so the elbow plates 24 may be rotated relative to the base 8 as is desired for the "hook lock" state.

In FIG. 8B, the "elbow lock" state, the sliding rachet 148 is moved (to the left) into contact with hook actuating pulley 94, the lock pin 152 is removed from the opening 156, and the lock pin 144 is moved into opening 140 in the elbow plate 24a to "lock" the elbow in fixed position. When the sliding rachet 148 is moved to the left (as will be described in more detail momentarily) it pushes an actuating pin 160 (to the left in FIG. 8B) to thereby push lock pin 144 into one of the openings 140 in the elbow plate 24a. In this state, when the elbow actuating pulley 82 is rotated, the hook actuating pulley 94 is also rotated to effect operation of the terminal device, for example, a hook.

Figure 9A:
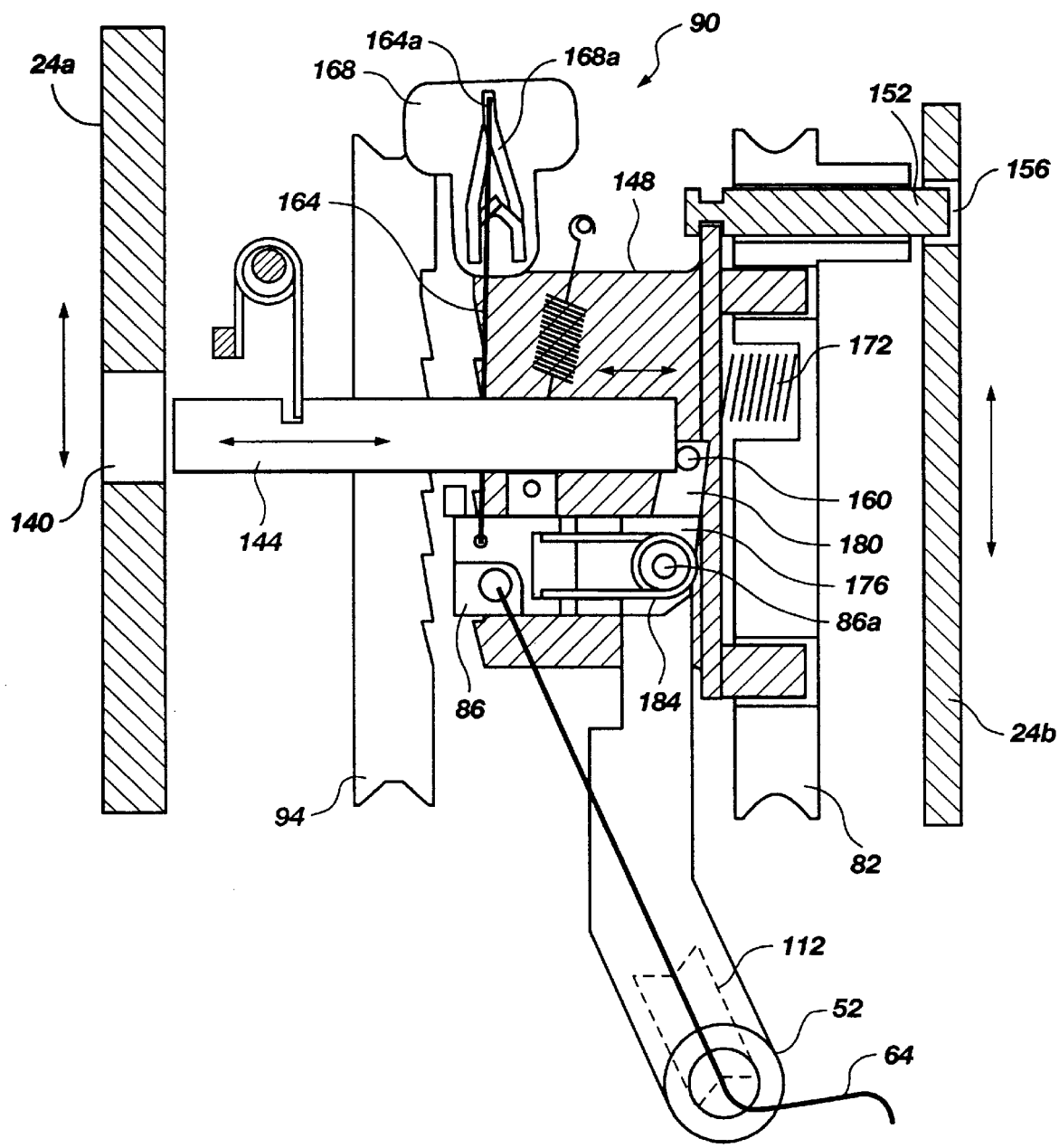
FIGS. 9A through 9E are top, fragmented, partially cross-sectional views of the locking mechanism of the prosthetic arm of the present invention, shown in various states of operation.

FIGS. 9A through 9D show different positions and stages of the state lock mechanism 90, showing changes from the "hook lock" state to the "elbow lock" state, and back again. The parts of the state lock mechanism 90 are also shown in FIG. 7, with corresponding parts having the same numbering. Referring to FIG. 9A, the state lock mechanism 90 is in the "hook lock" state in which lock pin 152 extends into opening 156 in elbow plate 24b and lock pin 144 is clear of any of the openings 140 in elbow plate 24a. Of course, sliding rachet 148 is also out of contact with hook actuating pulley 94. In this state, movement of the power cable 56 (not shown) will cause elbow actuating pulley 82 to rotate and this causes the elbow, namely elbow plates 24, to pivot relative to the base 8. In effect, the lock pin 152 which rotates with the elbow actuating pulley 82 acts against the sides of the opening 156 in the elbow plate 24b to cause the elbow plates 24 to pivot. Note, in this state, the location of the upper end 164a of a track wire 164, in a track 168a (in the form of a groove) defined in a track base 168.

Figure 9B:
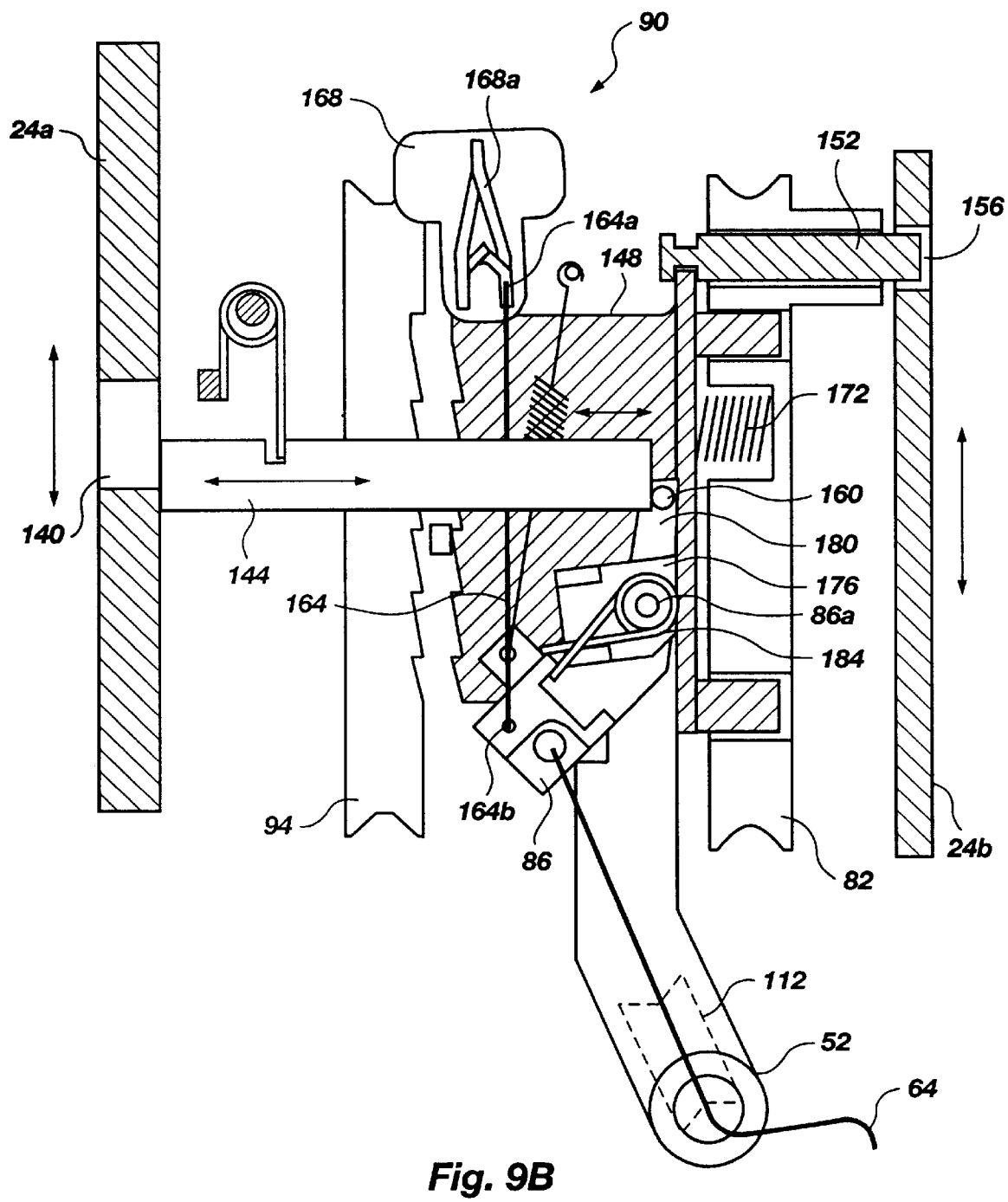

In FIG. 9B, the control cable 64 has been pulled to its maximum extent (downwardly) causing switch lever 86 to pivot downwardly as shown and this, in turn, causes track wire 164 (whose lower end 164b is coupled to the switch lever) to be pulled downwardly moving the upper end 164a of the track wire to move downwardly along a right leg of the track 168a to the bottom thereof, as shown. This frees an inner switch lever 176, which is mounted to pivot about the same axis 86a, as switch lever 86, to also pivot and allow actuating pin 160 (mounted to the inner switch lever 176 by actuating pin attachment arm 180) to pivot leftward and push against lock pin 144. In this position, the sliding rachet 148 is free to be forced leftward by a rachet spring 172 so that the rachet engages hook actuating pulley 94, except that lock pin 144 is not lined up with one of the openings 140. Thus, neither the lock pin 144 nor rachet 148 is allowed to move leftward, and lock pin 152 is not disengaged from opening 156.

Figure 9C:
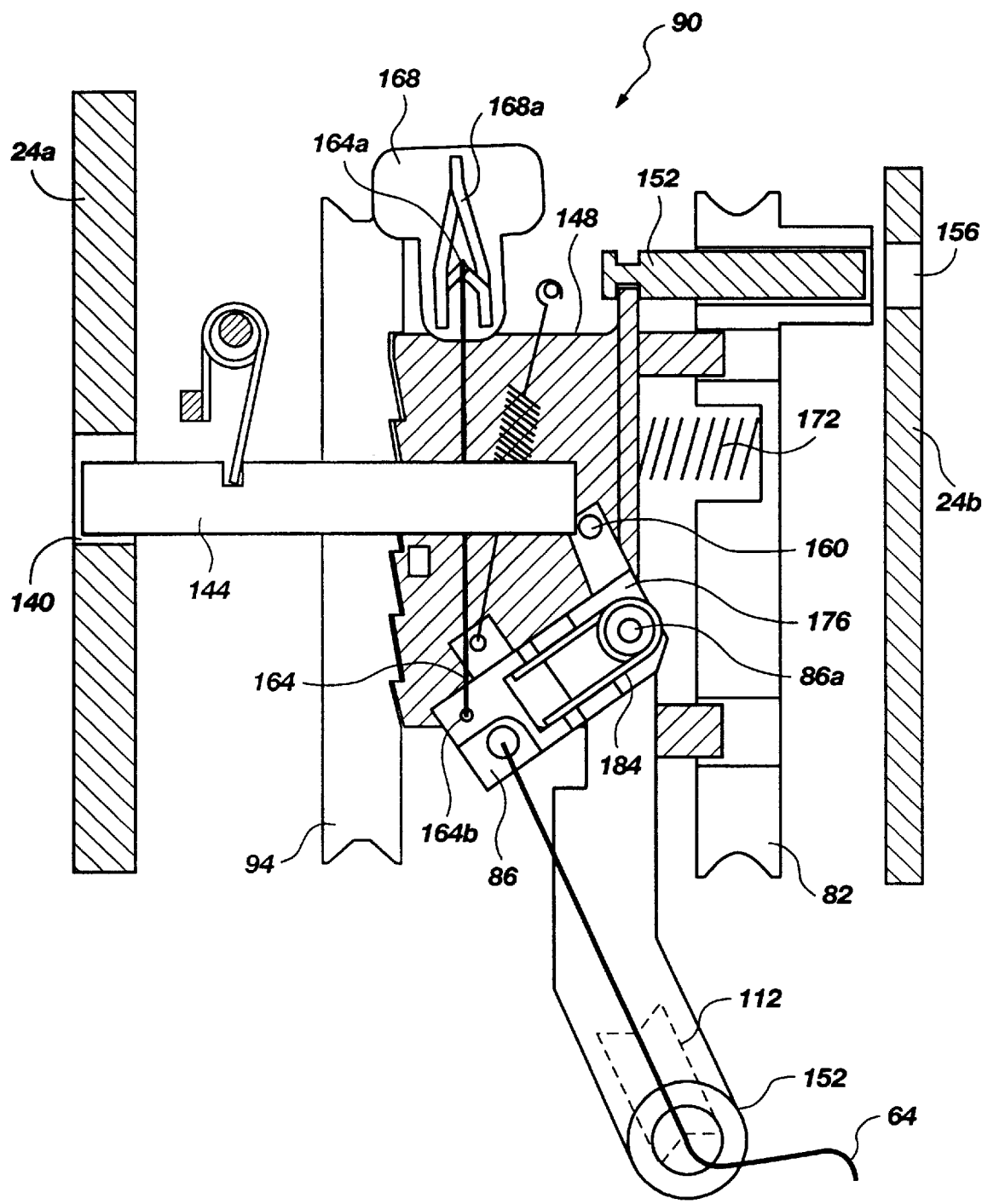

In FIG. 9C, the lock pin 144 has lined up with an opening 140 and so a switch loader spring 184 forces inner switch lever 176 to pivot into alignment with switch lever 86, forcing actuating pin 160 to move leftward and push lock pin 144 into the opening 140. Also, the rachet spring 172 forces the rachet 148 into contact with the hook actuating pulley 94. With movement of the rachet 148, lock pin 152 is pulled to the left and out of the opening 156. Note that the upper end 164a of the track wire 164 has now moved to the middle of the crossover portion of the track 168a, as a result of the release of the control cable 64, and this prevents the switch lever 86 from pivoting back to its initial position of FIG. 9A. The state of the state lock mechanism 90 of FIG. 9C is the "elbow lock" state.

Figure 9D:
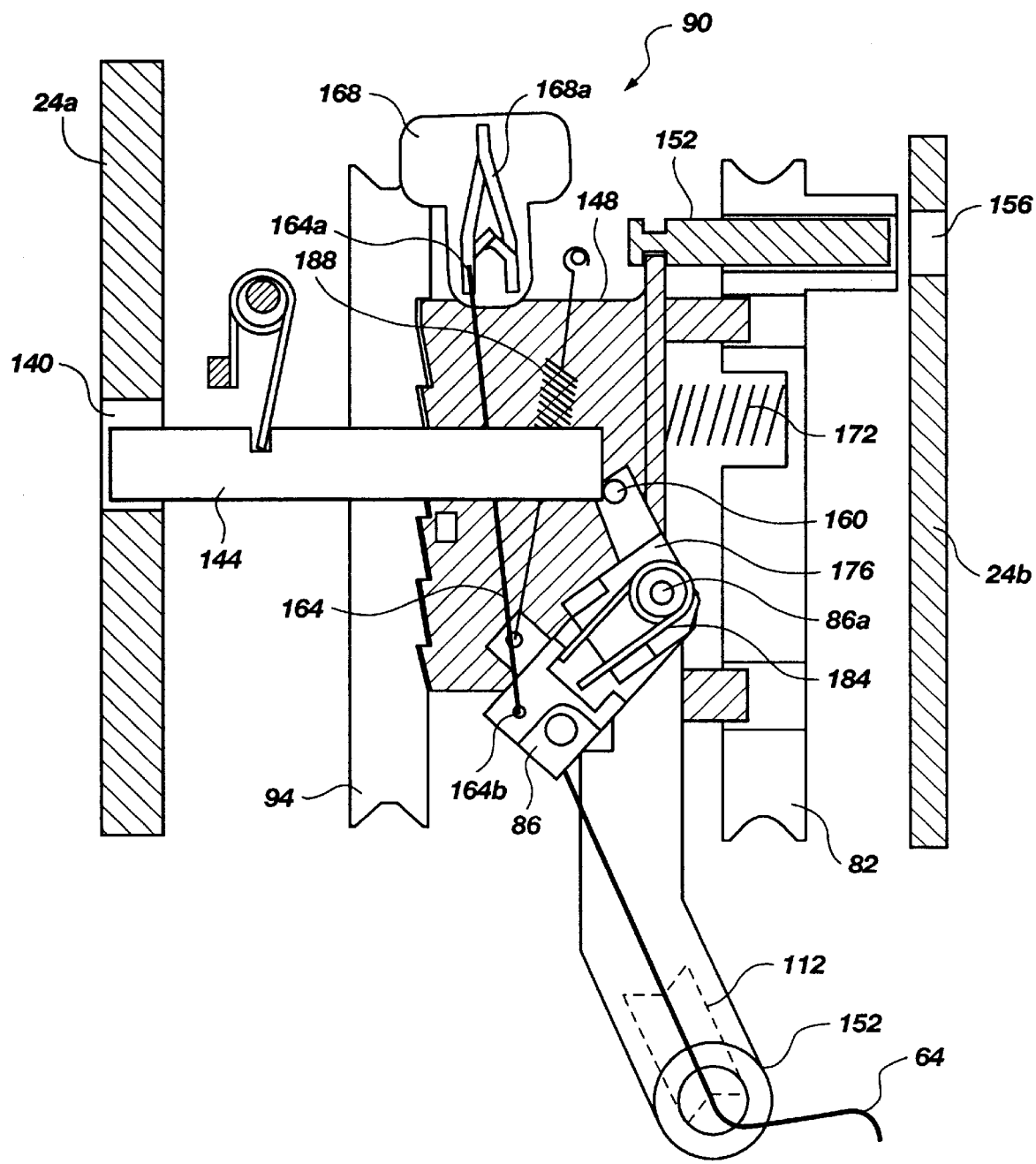

In FIG. 9D, the control cable 64 is again pulled to its maximum extent, pulling the switch lever 86 downwardly and moving the upper end 164a of the track wire 164 into the lower end of the left most leg of the track 168a as shown. Now, when the control cable 64 is released, the upper end 164a of the track wire 164 will be allowed to move up the left leg of the track 168a to the upper end of the track, as a result of switch lever return spring 188 pulling the switch lever 86, and thus the inner switch lever 176, back toward their starting positions.

Figure 9E:
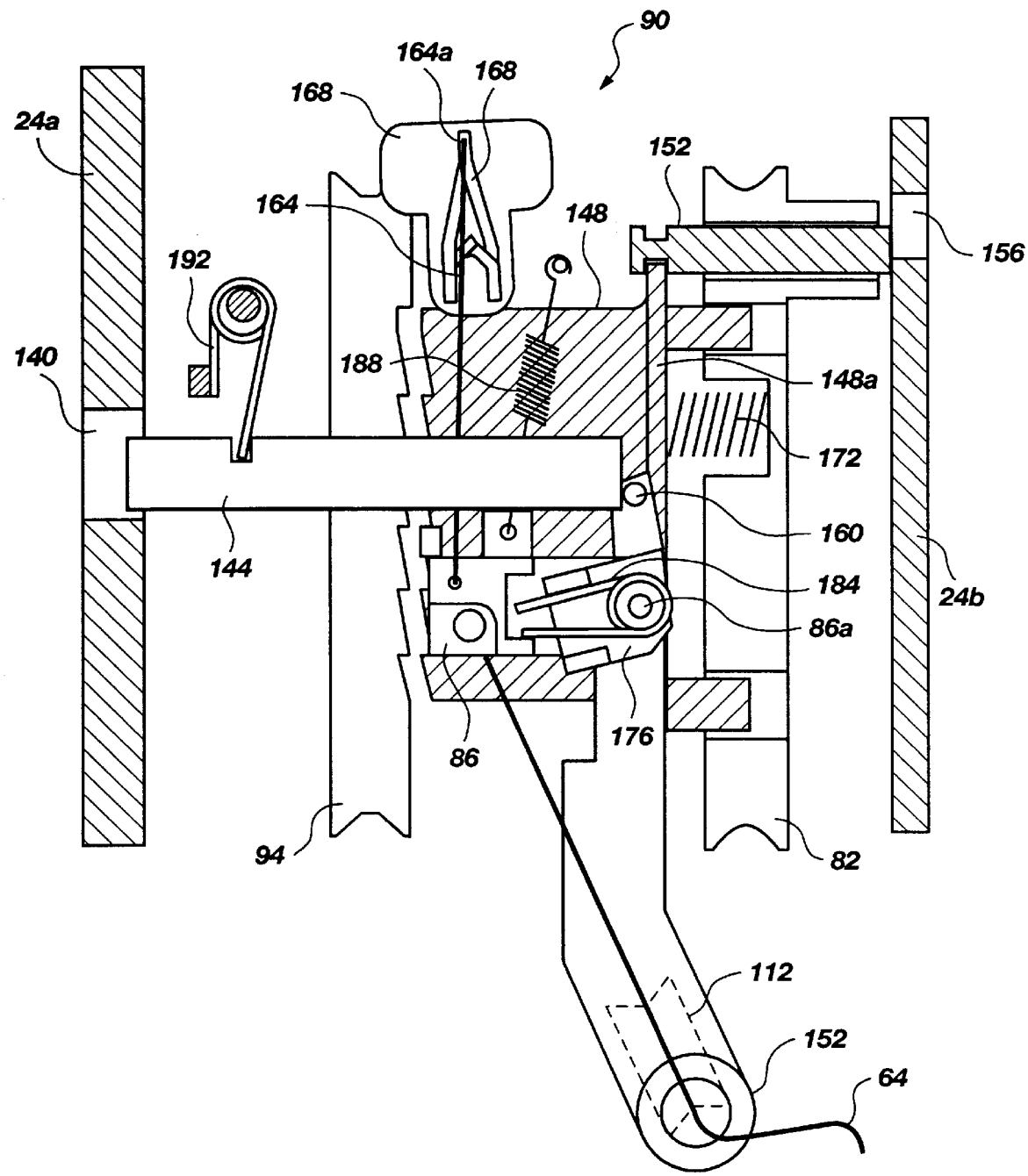

Referring now to FIG. 9E, the control cable 64 has been released and the switch lever 86 and inner switch lever 176 have pivoted clockwise so that actuating pin 160 has operated against lip 148a of the rachet 148 to move the rachet out of contact with pulley 94. A lock pin return spring 192 acts to move the lock pin 144 out of the opening 140 except that the lock pin 152 is not aligned with opening 156 and so neither the lock pin 144 can be fully withdrawn from the opening 140 nor the rachet 148 moved to its full rightmost excursion. Once lock pin 152 is aligned with opening 156, then switch loader spring 184 will move the inner switch lever 176 into alignment with switch lever 86, causing actuating pin 160 to act against the lip 148a of the rachet 148, to move the rachet to its rightmost excursion and move lock pin 152 into opening 156. Also, lock pin 144 will be moved completely out of the opening 140 by the lock pin return spring 192. As a result of this, the state lock mechanism 90 will now be in the "hook lock" state shown in FIG. 9A.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A prosthetic arm for fitting on an arm stump of an above-elbow amputee comprising base means for attachment to the arm stump, forearm means having a proximal end and a distal end, gripping means attached to the distal end of the forearm means for selectively opening or closing, elbow means for joining the proximal end of the forearm to the base means, and moveable to enable selectively pivoting the forearm means upwardly or downwardly, the elbow means comprising a pivot section pivotally attached to the base means, and an intermediate section extending downwardly and forwardly of the pivot section to a forward termination, said forward termination being connected to the forearm means, said intermediate section forming a bend at an angle of about 145 degrees from the pivot section, and control means responsive to body movements of the person for selectively locking the elbow means to prevent it from moving while allowing the gripping means to open or close, or locking the gripping means to prevent it from opening or closing while allowing the elbow means to move.

2. A prosthetic arm as in claim 1 further including spring means coupled between the forearm means and base means for providing a lift force to the forearm means.

3. A prosthetic arm as in claim 1 wherein said elbow means is fixedly attached to the proximal end of the forearm means, and pivotally attached to the base means, and wherein said control means includes state locking means selectively manipulable to either an elbow means lock state, in which the elbow means is prevented from pivoting with respect to the base means, or a gripping means lock state, in which the gripping means is prevented from opening, control cable means coupled to the state locking means for selectively manipulating the state locking means to either the elbow means lock state or the gripping means lock state, and power cable means coupled to the elbow means and gripping means, and which, when operated, causes pivoting of the elbow means with respect to the base means when the state locking means is in the gripping means lock state, and causes opening/closing of the gripping means when the state locking means is in the elbow means lock state.

4. A prosthetic arm as in claim 3 further comprising an elbow means pulley mounted to rotate when the power cable means is operated, gripping means pulley mounted to rotate when the elbow means pulley is rotated and the state locking means is in the elbow means lock state, gripping means cable coupled between the gripping means pulley and the gripping means to cause the gripping means to open when the gripping means pulley is rotated, and wherein said state locking means includes lock means manipulable by the control cable means to selectively lock the elbow means pulley to the elbow means to cause the elbow means to pivot with respect to the base means as the elbow means pulley is rotated, or lock the elbow means pulley to the gripping means pulley to cause the gripping means pulley to rotate as the elbow means pulley is rotated.

5. A prosthetic arm as in claim 4 further including first shoulder strap means for placement on the shoulder and back of a person, and second shoulder strap means also for placement on the shoulder and back of the person, and wherein said control cable means is coupled to the first shoulder strap means to manipulate the lock means by movement of the person's shoulder in a shrug, and wherein said power cable means is coupled to the second shoulder strap means to operate when the person moves a shoulder.

6. A prosthetic arm as in claim 4 further including a tension take-up pulley means rotatably disposed so that the gripping means cable is wrapped thereabout, for pushing against the gripping means cable to remove slack therein.

7. A body-powered prosthetic arm mountable on an arm stump of a person, comprising an attachment member having a receptacle end for fitting on an arm stump socket device, and a connector end, a forearm section having a proximal end for pivotally attaching to the connector end of the attachment member to pivot upwardly or downwardly, and a distal end, said forearm section extending downwardly and forwardly from the attachment member through a first length and then forwardly through a second length forming a bend, the second length being at an angle of about 145 degrees with respect to the first length, terminal device means mounted on the distal end of the forearm section and operable to selectively open or close, locking means responsive to movement of a cable for selectively locking and preventing pivoting of the forearm section or locking and preventing operation of the terminal device means, first cable means coupleable to the body of the person, and moveable when the body is moved to thereby cause selective locking of the locking means, and second cable means coupleable to the body of the person, and to the forearm section and terminal device means, said second cable means being moveable when the body is moved to thereby cause the forearm section to pivot if the terminal device means is locked, and to cause the terminal device means to operate if the forearm section is locked.

8. The prosthetic arm of claim 7 further including resilient means coupled between the attachment member and the forearm section for providing a lift force to the forearm section.

* * * * *